United States Patent
Bonne et al.

(10) Patent No.: US 6,306,083 B1
(45) Date of Patent: *Oct. 23, 2001

(54) INTEGRATED ILLUMINATION AND IMAGING SYSTEM

(75) Inventors: Ulrich A. Bonne, Hopkins; James A. J. Holroyd, Edina; David R. Wulfman, Minneapolis; David H. Jeffrey, Mounds View; Arthur G. Erdman, New Brighton, all of MN (US)

(73) Assignee: Micro Medical Devices, Inc., Cleveland, OH (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/213,950

(22) Filed: Dec. 17, 1998

Related U.S. Application Data

(63) Continuation of application No. 08/890,803, filed on Jul. 11, 1997, now Pat. No. 6,013,025.
(60) Provisional application No. 60/022,023, filed on Jul. 11, 1996.

(51) Int. Cl.[7] ................................ A61B 1/07; G02B 6/06
(52) U.S. Cl. ......................... 600/182; 600/178; 385/117; 362/574
(58) Field of Search ................................ 600/160, 178, 600/181, 182; 385/116–119, 36, 115; 359/196, 220, 226, 386, 389; 362/232–234, 238, 241, 247, 554, 556, 574, 557

(56) References Cited

U.S. PATENT DOCUMENTS

| | | | |
|---|---|---|---|
| 1,692,554 | * 11/1928 | Leiter | 600/160 |
| 2,128,394 | * 8/1938 | Berek | 359/389 |
| 3,010,357 | * 11/1961 | Hirschowitz | 600/182 |
| 3,413,067 | * 11/1968 | Froio | 600/160 |
| 3,535,018 | * 10/1970 | Vasilatos | 385/36 |
| 3,589,795 | * 6/1971 | Miyazaki | 385/115 |
| 3,602,640 | * 8/1971 | Maillet et al. | 362/232 |
| 3,724,922 | * 4/1973 | Jones | 600/178 |
| 3,780,630 | * 12/1973 | Nakajima | 362/574 |
| 4,135,791 | * 1/1979 | Govignon | 385/115 |
| 4,425,599 | * 1/1984 | Rieder et al. | 600/181 |
| 4,938,205 | * 7/1990 | Nudelman | 600/182 |
| 4,943,137 | * 7/1990 | Speer | 362/234 |
| 4,945,895 | * 8/1990 | Takai et al. | 600/182 |
| 5,061,995 | * 10/1991 | Lia et al. | 600/182 |
| 5,126,877 | * 6/1992 | Biber | 359/389 |
| 5,432,876 | * 7/1995 | Appeldorn et al. | 385/31 |
| 5,463,534 | * 10/1995 | Raven | 362/234 |
| 5,513,286 | * 4/1996 | Easley | 385/116 |
| 5,823,942 | * 10/1998 | Toida | 600/160 |

FOREIGN PATENT DOCUMENTS

WO 91/15793  10/1991  (WO).

* cited by examiner

*Primary Examiner*—John P. Leubecker
(74) *Attorney, Agent, or Firm*—Fish & Richardson P.C.

(57) ABSTRACT

A fiber optic endoscope which uses a bundle of coherent fiber to convey both an optical image in one direction and illumination light in the other direction. A fraction of the optical fibers are used for the illumination, and others of the fibers are used for the image. Notched fibers can be used for the illumination.

6 Claims, 17 Drawing Sheets

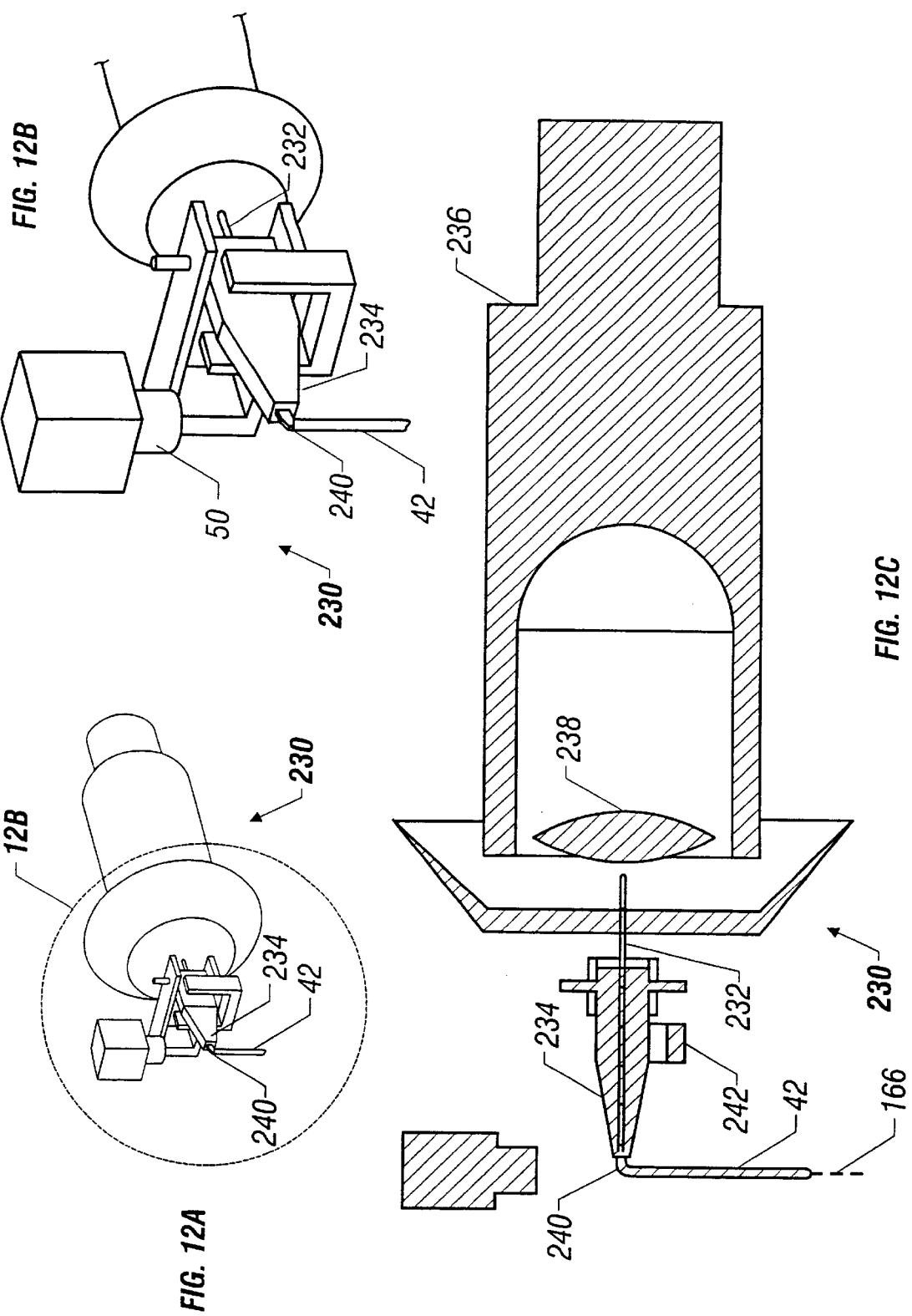

INTEGRATED ILLUMINATION AND IMAGING SYSTEM

This is a continuation of application Ser. No. 08/890,803 filed on Jul. 11, 1997, now U.S. Pat. No. 6,013,025. This application claims benefit to provisional application 60/022,023 filed on Jul. 11, 1996.

FIELD OF THE INVENTION

The present application describes an integrated illumination and imaging system. In one form, these concepts are particularly adapted for use with an endoscope which has the capacity to illuminate a site of investigation and transmit an image of that site by an-image carrying transmission medium.

BACKGROUND OF THE INVENTION

Micro invasive surgery has a goal of minimizing the amount of damage caused during surgery. Some surgical procedures, for example, can be obviated by using an endoscope through a small incision. The size of the incision, therefore, depends on the size of the endoscope. One important feature of an endoscope, therefore, is its size. Since many endoscopes require a separate light guide, this increases the size of the endoscope.

Current endoscopes often use some type of illumination bundles or light guides to couple light to a site of viewing. The site of viewing is then imaged by appropriate receiving of the coupled light that is reflected by the area of the viewing site.

The present application describes a system that eliminates the need for a separate light guide and thereby reduces the requisite, probe dimensions for a desired image size. Like current endoscopes, endoscopes using this new technique are safe to introduce into the human body for use in minimally invasive surgery. One application of this device is in the area of root canal procedures in dentistry, although this system could similarly be used in other kinds of surgery.

International Patent Application No. WO 91/15793, by Acosta, et al., discloses an endoscope in which light is transmitted to and from an anatomical site. One embodiment of the Acosta, et al. endoscope includes a plastic optical fiber assembly in which light is transmitted to the distal end of the endoscope along the periphery of the fiber assembly itself. Imaging light is transmitted back to the proximal end through a central multi-fiber bundle.

Another embodiment of the Acosta, et al. application discloses a plastic optical fiber assembly in which illuminating light is directed through a predetermined portion of the multi-fiber bundle. The balance of the bundle is.dedicated to transmitting imaging light.

An alternative embodiment of the Acosta, et al. Application described an endoscope in which a beam splitter directs light across the entire face of the multi-fiber bundle. The returning imaging light is also transmitted through the entire crosssectional area of the bundle through the beam splitter to a viewing portion of the endoscope, which is proximal to the beam splitter.

SUMMARY OF THE INVENTION

The inventors recognized a need for an illumination and imaging device which does not require a predetermined subset of fibers to be dedicated to transmitting either illuminating or imaging light. There is a further need for a self-filtering illumination and imaging device in which variable and dynamically changing portions of the multi-fiber bundle transmit either illuminating or imaging light.

An illuminating and imaging system of this system enables alternate functions of illuminating and imaging transmissions to be separately applied to non-dedicated, dynamically alterable subsets of the multi-fiber image bundle;

will function using any type of image carrying transmission medium with partitioned or pixeled capability;

enables all fibers of a multi-fiber image bundle to serve in either illumination or image transmission;

needs no separator or additional cladding between fiber portions of the image bundle;

non-simultaneously uses all portions of a fiber optic bundle for both illumination and image transmission; and functions as a self-filtering system due to the placement of the light emitting element with respect to the fibers which are transmitting illuminating light, thereby eliminating a sensation of glare when the image is viewed or recorded.

Main advantages to this system over those proposed previously include:

1. Removal of light guides to make the bundles smaller and therefore less invasive;
2. Reduction of the complexity of a given endoscope, which reduces the difficulty and the cost of its manufacture; and
3. Removal of the light guides allows the entirety of an endoscope's cross sectional area to be devoted to the image bundle. Therefore, an endoscope operating by means of this proposed system can produce a higher resolution image than conventional endoscopes of equal cross-sectional area.

We have considered multiple methods of implementing this dual function bundle. They include the following:

1. Stationary Light Channeling
   Channeling Above Bundle
2. Stationary Light Channeling
   Channeling Within Bundle
3. Oscillating Light Channeling
4. Rotary Light Channeling
   Rotation on Axis with Bundle
   Light Sources Stationary
5. Rotary Light Channeling
   Rotation on Axis with Bundle
   Light Sources Rotate with Channeling Devices
6. Rotary Light Channeling
   Rotation on a Parallel Axis with Bundle Axis
   Light Sources Stationary
7. Cantilever Beam
   Bending within the illumination plane
   Light Source(s) Stationary

BRIEF DESCRIPTION OF THE DRAWINGS

These and other aspects of the invention will be described with reference to the accompanying drawings, wherein:

FIG. 12 shows a Cantalever beam with fiber like channels;

DESCRIPTION OF THE PREFERRED EMBODIMENTS

Figure 1A:
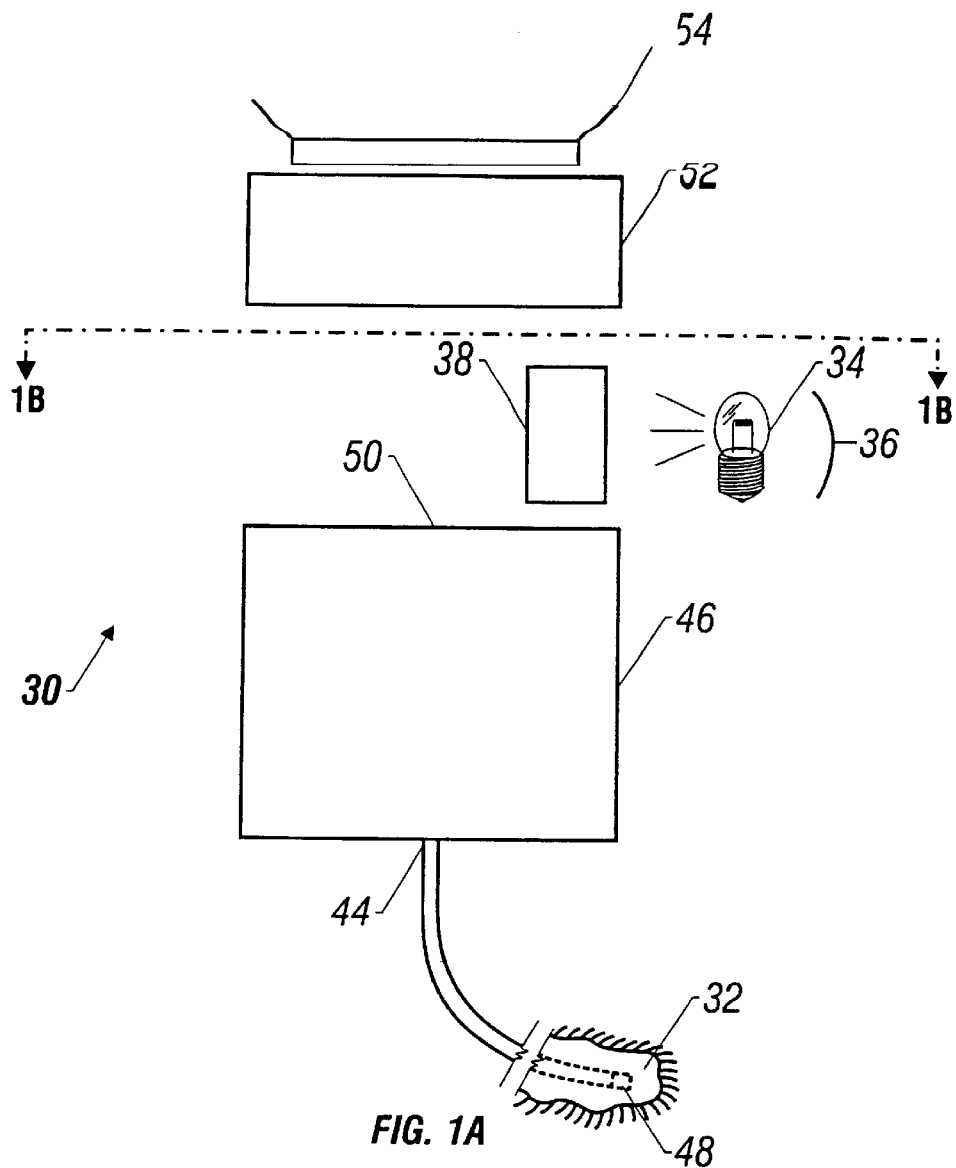
FIG. 1 shows a general drawing of the endoscopic device.
Figure 1B:
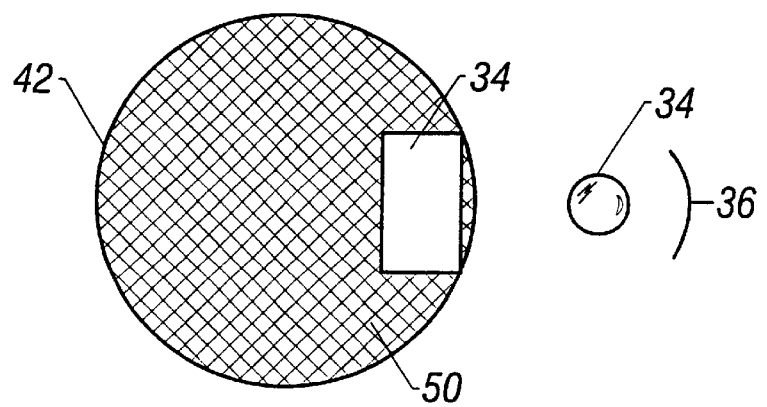

An endoscope 30 of the preferred embodiment is depicted in FIG. 1 as imaging an anatomical site 32 whose image is desired to be detected. The system operates by discretely projecting radiation, e.g., light, through a portion of a light transmission device. The preferred embodiment uses the fibers 42 in the image bundle 44 of a fiber optic endoscope 30. This system operates to remove the necessity of separate light guides for illumination. The outer surface of the image bundle represents the hole size that needs to be made in order to insert the endoscope device.

A light illuminating device is effected by gathering light from external light source 34 by light focusing device 36, and coupling that light into light channeling device 38. Light is then focused on a specific location or locations of image bundle 42 of endoscope 30 at its proximal end 44. Light focusing from light channeling device 38 may be incorporated directly into image bundle 42, or may be accomplished by a gradient index (GRIN) lens 46 mounted to the proximal end 44 of fiber optic bundle 44. The exposed portions of the bundle then carry light from the proximal end to distal end 48 of endoscope 30, where the accumulated light then illuminates the site of interest 32. The remainder 50 of bundle 42 having its fibers unexposed to light at the proximal end, collect light reflected from the surfaces in the site of interest and carry it to proximal end 44 of endoscope 30. That light is then magnified by camera optics 52 and collected by recording device 54, such as a digital video camera.

Embodiment 1. Stationary Light Channeling

Figure 2A:
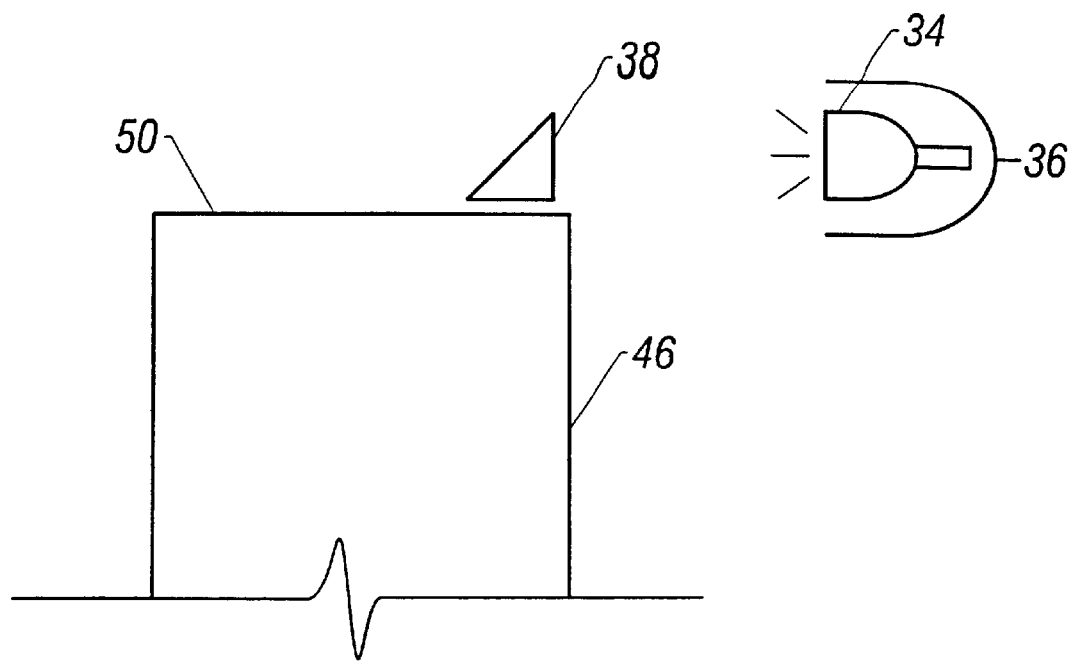
FIGS. 2A and 2B show a first embodiment operating to channel the light above the bundle.
Figure 2B:
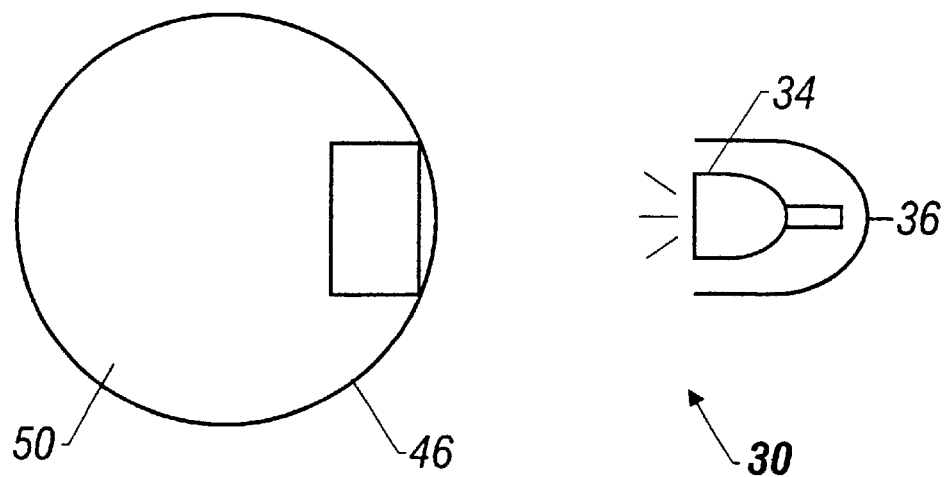

This first embodiment is shown in FIGS. 2A and 2B, and uses the operation of channeling above bundle.

Endoscope 30 includes light channeler 38 permanently mounted above the portion of the GRIN 46 or the image bundle. Light channeler is dedicated to illumination. Light from external source 34 is focused by focusing device 36 and aimed at light channeler 38, which then transmits this light onto the portion 56 of the bundle over which it is located. In this version of the device, section 56 of the image bundle located below the channeler 38 is permanently dedicated to illumination. The image receiving device records an image proximate distal end 48 of bundle 42 partially obscured by light channeler 38.

Embodiment 2.

Figure 3A:
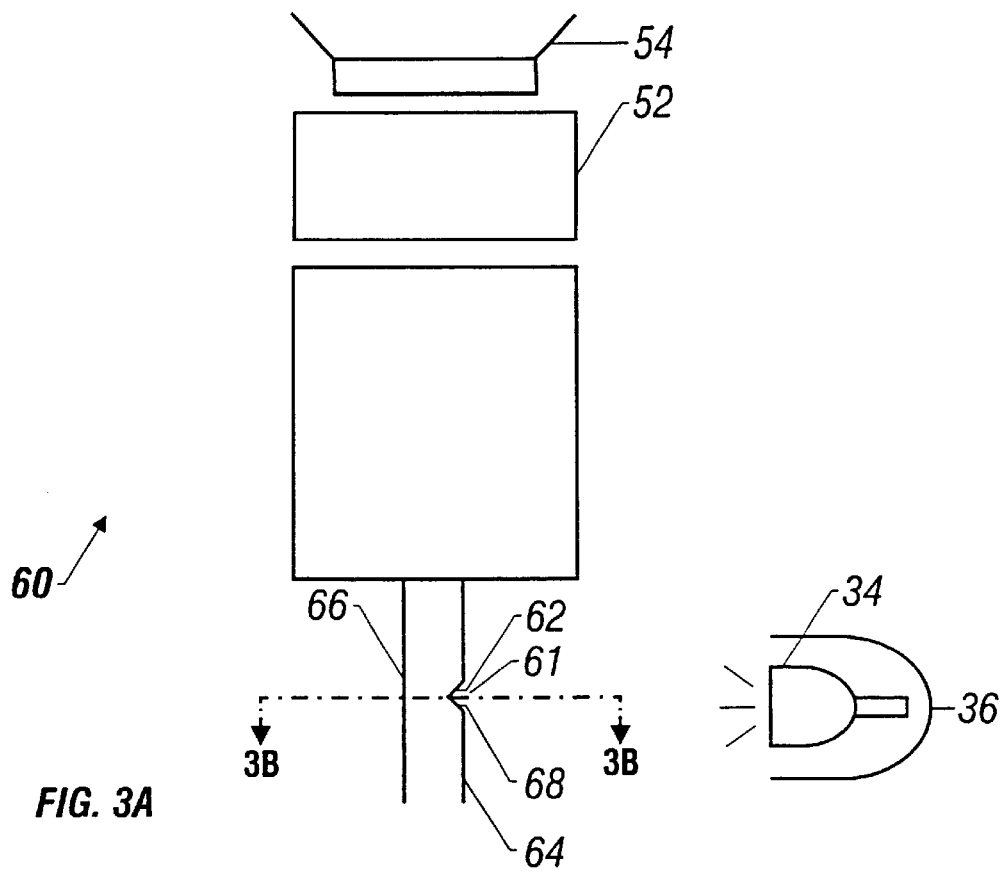
FIGS. 3A and 3B shows a device which channels with the bundle.
Figure 3B:
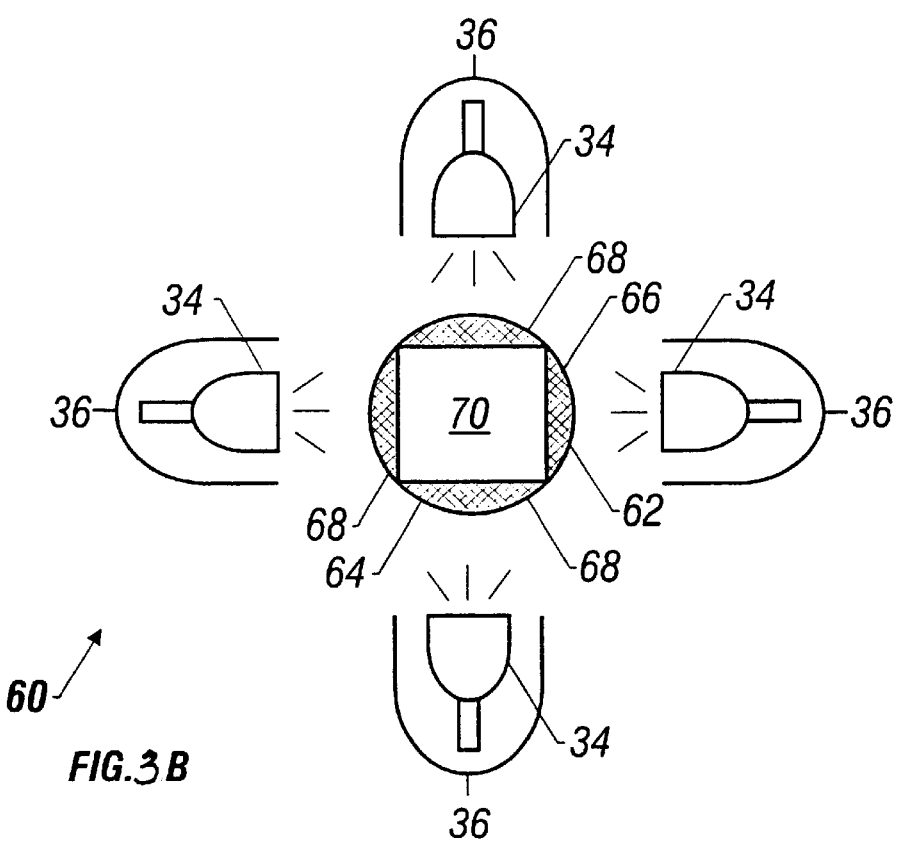

The second embodiment uses stationary light channeling, and is shown in FIGS. 3A and 3B. This operates to carry out channeling with the bundle.

Endoscope 60 includes channeling device 61 integrated within the bundle. Channeler 61 is formed by notch 62 cut into outside wall 64 of bundle 66. Notch 62 has the proper geometry to receive light from direct light source 34 and divert the light toward the distal end of bundle 66. Light received from notch 62 travels through bundle 66. This system uses the exposed fibers 68 as being permanently dedicated to illumination. FIG. 3B shows that light channeling may be accomplished by one or more notches 62 placed in bundle wall 64, which expose one or more sets of fibers 68 to illuminating light.

Embodiments 1 and 2 differ from current endoscope technology by eliminating the need for light guides for illumination. This is done by permanently dedicating a section of the image bundle fibers to serve the function of illuminating the sight of examination at the distal end of endoscope.

The remaining embodiments, unlike embodiments 1 and 2, use light channeling devices are in motion with respect to the fiber optic bundle they are illuminating, and the device used to record the image (the camera). The channelers at a given instant in time obscure the bundle from view as do those in embodiment 1, yet the portion they obscure is not the same over time. The motion of the channeler(s) is fast enough that the recorded image appears like an image seen through a propeller or ventilation fan in motion.

At any given moment, the portion of the image bundle exposed to the light channeling device may range from 100% to 0%. Equivalently, at any given moment, the portion of the image bundle exposed to the optical recording device may range from 0% to 100%, but in practice will be less than the full range of the multiplexed use of the device, the optical range between about 30% and 70%.

As will be appreciated, the oscillation or rotation rates of the remaining embodiments lie within the range of the sampling rate of the detector.

Embodiment 3. Oscillatory Light Channeling

Figure 4:
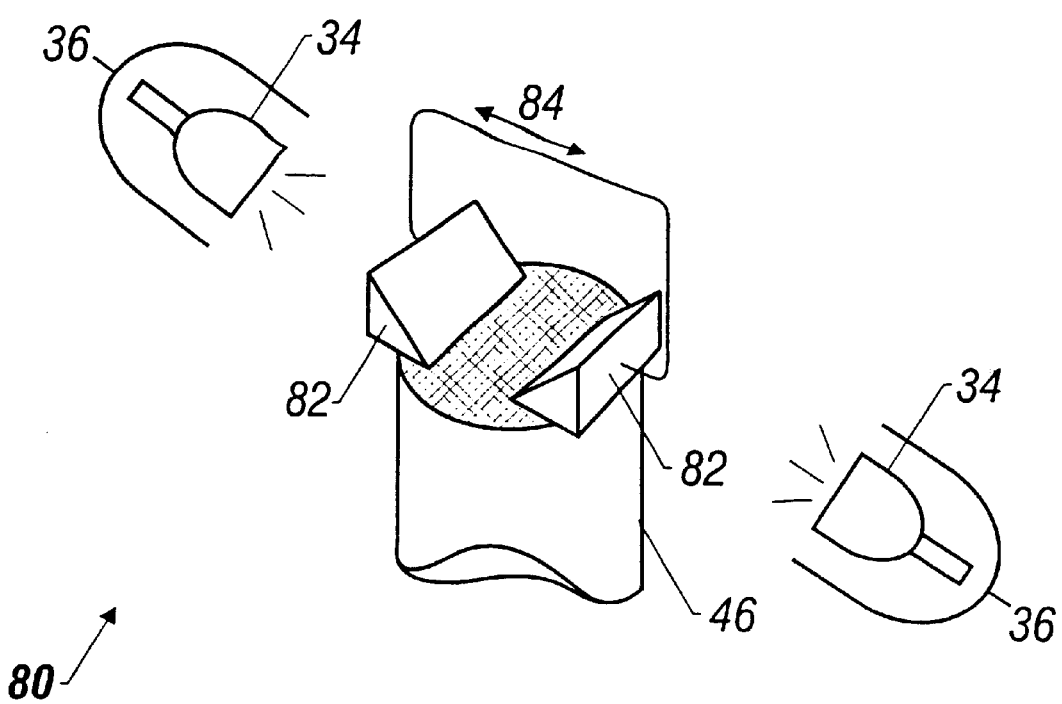
FIG. 4 shows an endoscope with an image bundle that alternates functions between illumination and image transmission.

Endoscope 80 shown in FIG. 4 differs from embodiments 1 and 2 in that sections of GRIN lens 46, hence image bundle 42, alternate functions between illumination and image transmission. One or more light channelers 82 oscillate as shown by arrow 84. At a given instant, whatever portion of the bundle is located directly below the light channeler transmits light to a site of interest for illumination, while at other times the same portion provides image transmission. As with embodiments 1 and 2, the channeler receives light from a fixed external light source.

Embodiment 4. Rotary Light Channeling

Figure 5:
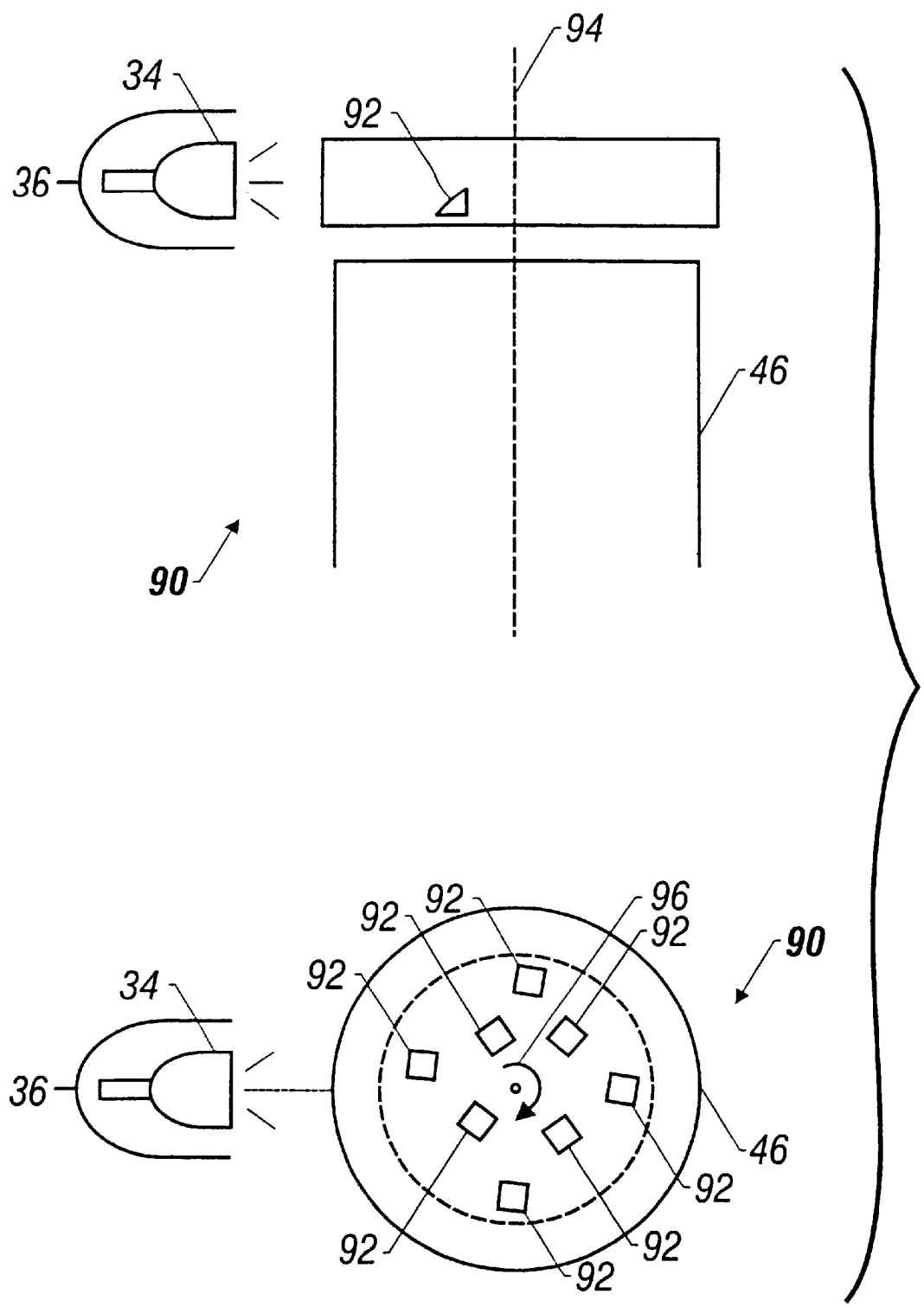
FIG. 5 shows a system rotating on axis with the bundle.

This embodiment is shown in FIG. 5. The system described operates to carry out rotation on Axis with Bundle, and using stationary light Sources.

Endoscope 90 employs one or more reflectors (or channelers) 92 rotating about the bundle axis 94 as shown by arrow 96. Rotation of reflectors 92 in this manner provides for illumination to different sections of GRIN lens 46, hence image bundle 42 (not shown), at different times. In this embodiment, light is provided by one or more fixed external sources appropriately aimed and focused onto the reflectors 92.

Embodiment 5. Rotary Light Channeling

Figure 6:
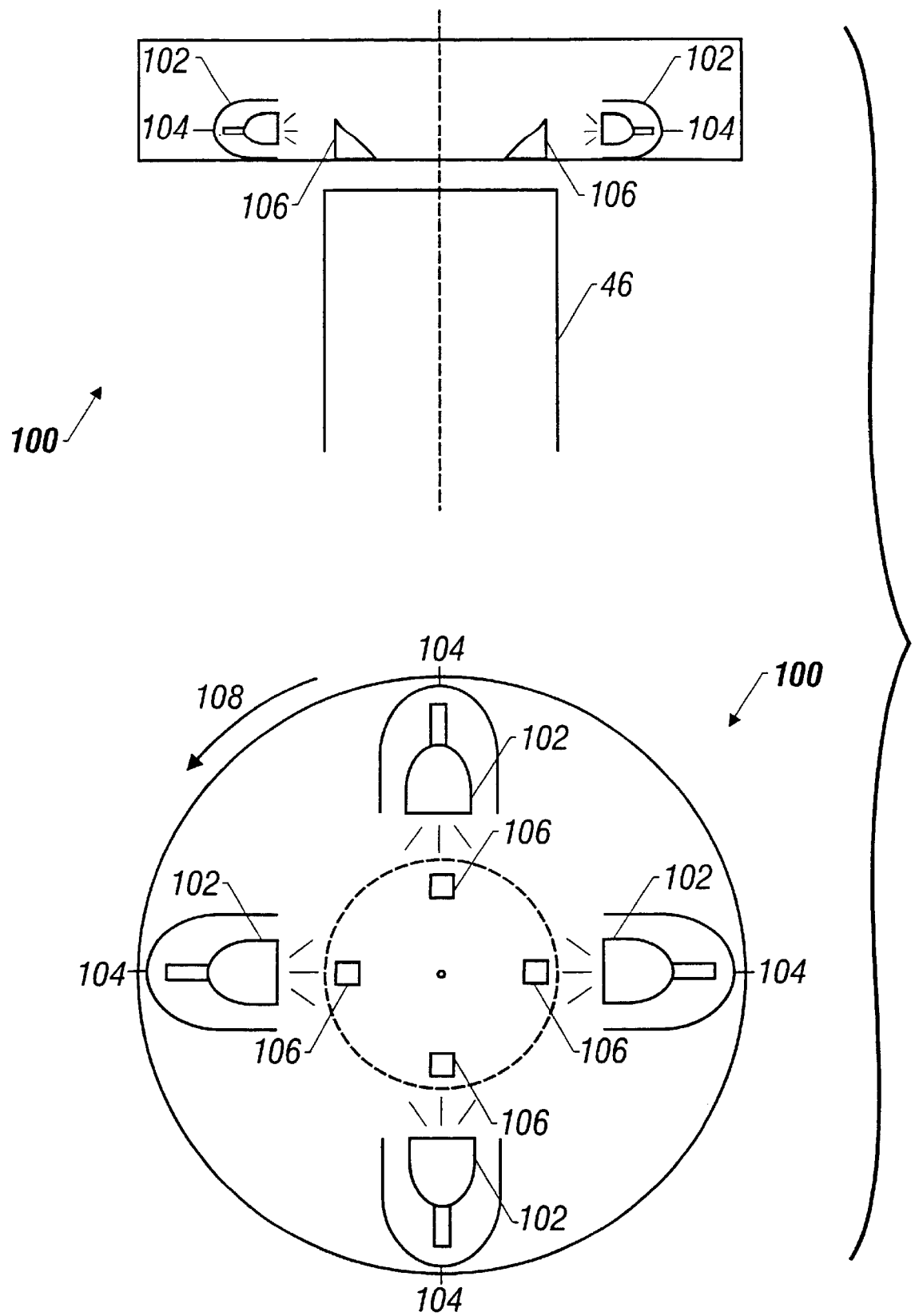
FIG. 6 shows an embodiment with additional light sources that rotate.

FIG. 6 shows this embodiment using rotation on Axis with Bundle, and light Sources Rotate with Channeling Devices.

In endoscope 100, one or more light sources 102 are dedicated to channelers 106. That is, these endoscopes rotate as depicted by arrows 108 along with channelers 106 over GRIN lens 46, hence bundle 42, out of the range of view of the image recording device (not shown).

Embodiment 6. Rotary Light Channeling

Figure 7:
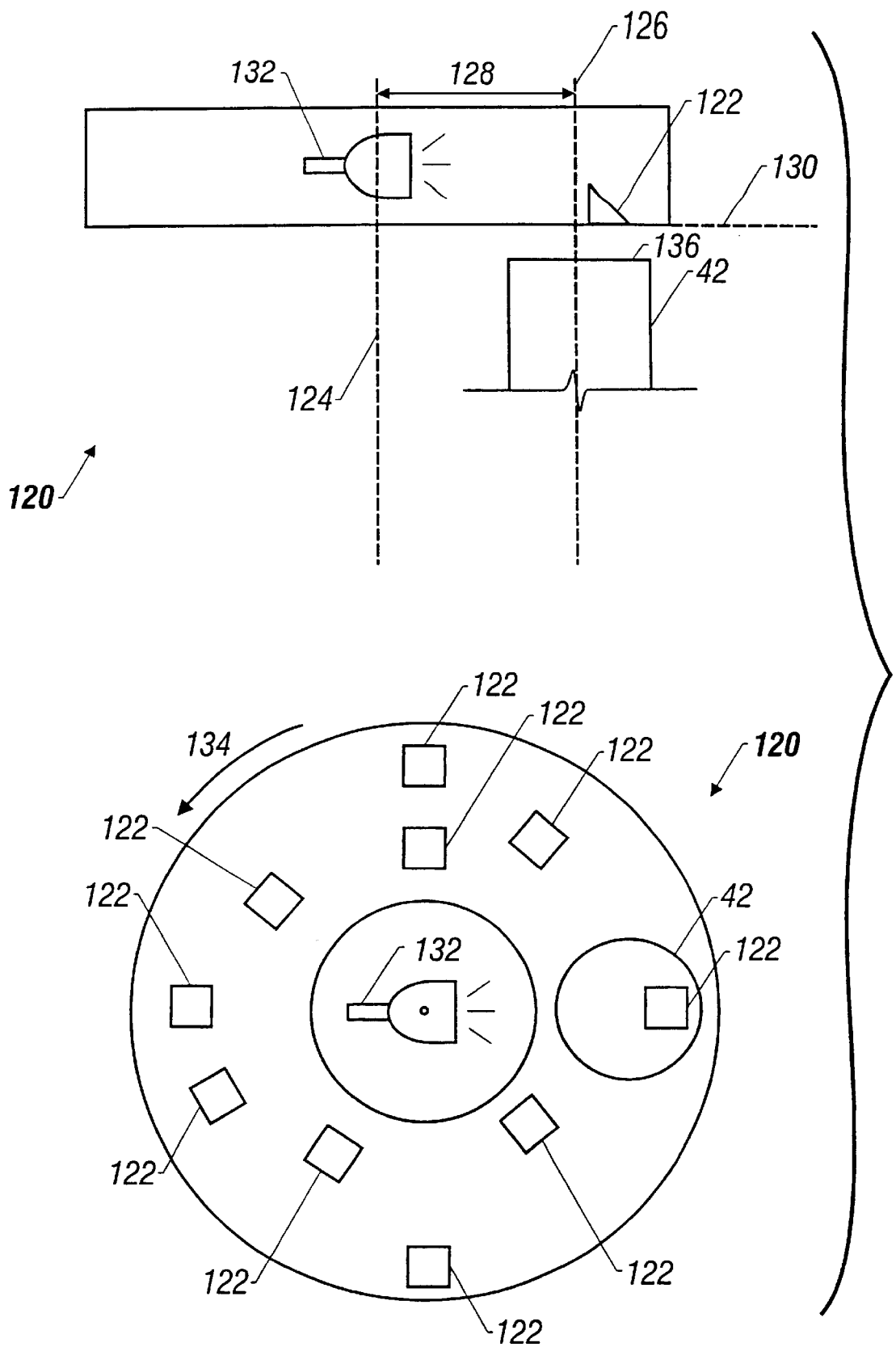
FIG. 7 shows an embodiment operating to rotate on a parallel axis to the bundle axis.

FIG. 7 shows this embodiment using Rotation on a Parallel Axis with Bundle Axis, with stationary light Sources Stationary endoscope 120 includes channelers 122 which rotate about axis 124 which is parallel to axis 126 of image bundle 42, yet offset by some fixed distance 128. Illumination plane 130 is located some fixed distance above image bundle 42 and a fixed distance below the image recording device (not shown). A single light source 132, located at a predetermined location within illumination plane 130, is aimed at image bundle axis 126. As a channeler 122 passes over image bundle 42 in its orbital travel 134, channeler 122 collects light from the source 132 and directs the light onto portion 136 of bundle 42 over which channeler 122 is traveling.

Embodiment 7. The Cantilever Beam

Figure 8:
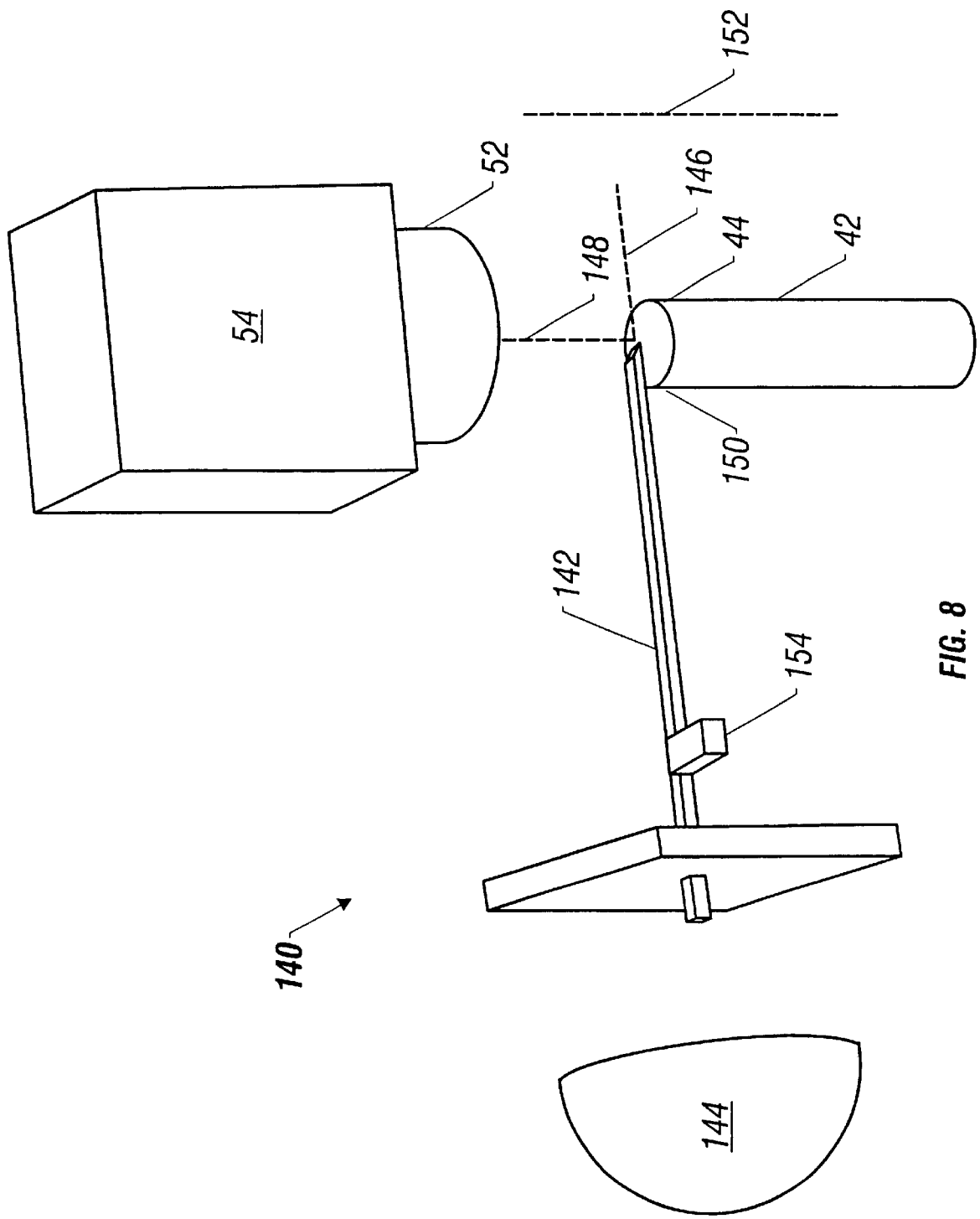
FIG. 8 shows a Cantalever beam system.

The concept of the cantilever beam, which bends with the illumination plane using a stationary light Source, is shown in FIG. 8.

Endoscope 140 uses a cantilever light beam 142 which extends from light source 144. Beam 142 cyclically deflects light from its neutral axis 146 into proximal end 44 of image bundle 42. The path of deflection 150 exists within illumination plane 152 and intersects with bundle axis 148 between proximal end 44 of image bundle 42 and recording device 54. Beam 142 acts as a carrier for a light channeler located at the bundle axis (not shown) or may serve as a light channeler itself. Light source 144, located at the fixed end of beam 142, is aimed at the light channeler if a light channeler is present. An illumination path originates at light source 144, travels along or through beam 142 to the light channeler, and enters the section of the bundle 42 directly below the channeler. As the beam bends back and forth over proximal end 44 of image bundle 42, different portions of image bundle 42 are exposed to the channeler at different points in time. Like embodiments 3–6, this arrangement provides the opportunity for portions of the image bundle to function at one instant in time as an element which illuminates light transmission from the proximal to distal end of the bundle and as a device for imaging light transmission from the distal end to the proximal end of the bundle, at another instant in time. Beam oscillation is accomplished by means of a driver, or actuator 154, or by the beam 142, itself, depending on the actuation implementation chosen.

Actuators for oscillatory motion include, but are not limited to, slider-crank mechanisms, piezoelectric vibratory actuators, self-actuating cantilever light beams, and exploitation of intermittent magnetic or electric fields. For rotary motion, actuators include but are not limited to direct drive rotary motors, gear transmissions driven from rotary motors, servo motors, and air drive systems generated either from a fan or from natural convection currents generated from the light source.

Light channelers include but are not limited to the following devices: prisms, fiber optic light guides, transparent disks in which are machined facets which function as prisms, transparent disks on which are discreetly placed patches of refractive film causing light traveling through the disk to divert out of the disk in the desired direction.

The following embodiment descriptions are examples of how certain light channelers could be implemented. Implementations of these light channelers are not limited to the embodiments illustrated below.

Figure 9:
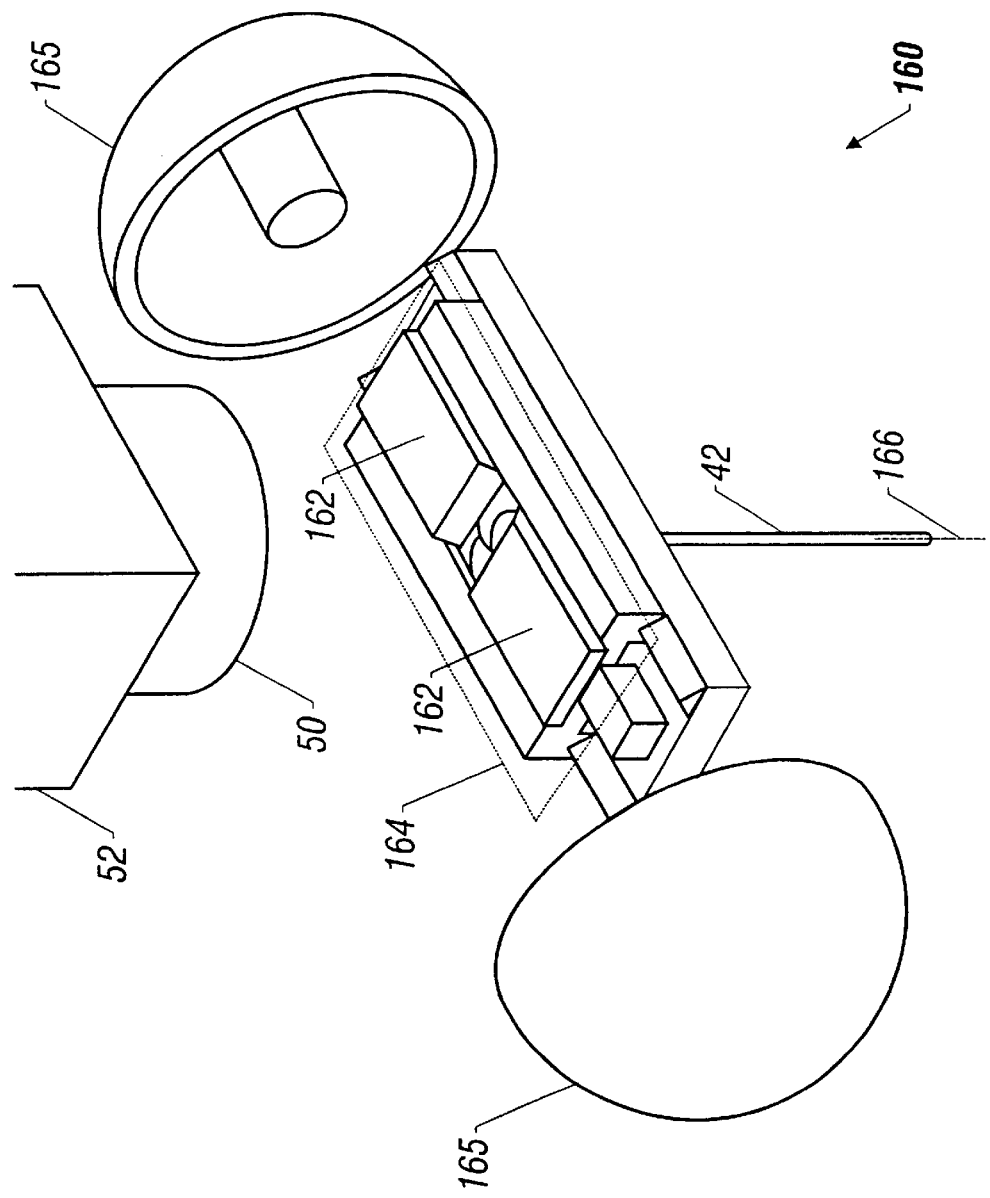
FIG. 9 shows an endoscope with prisms.
Figure 10A:
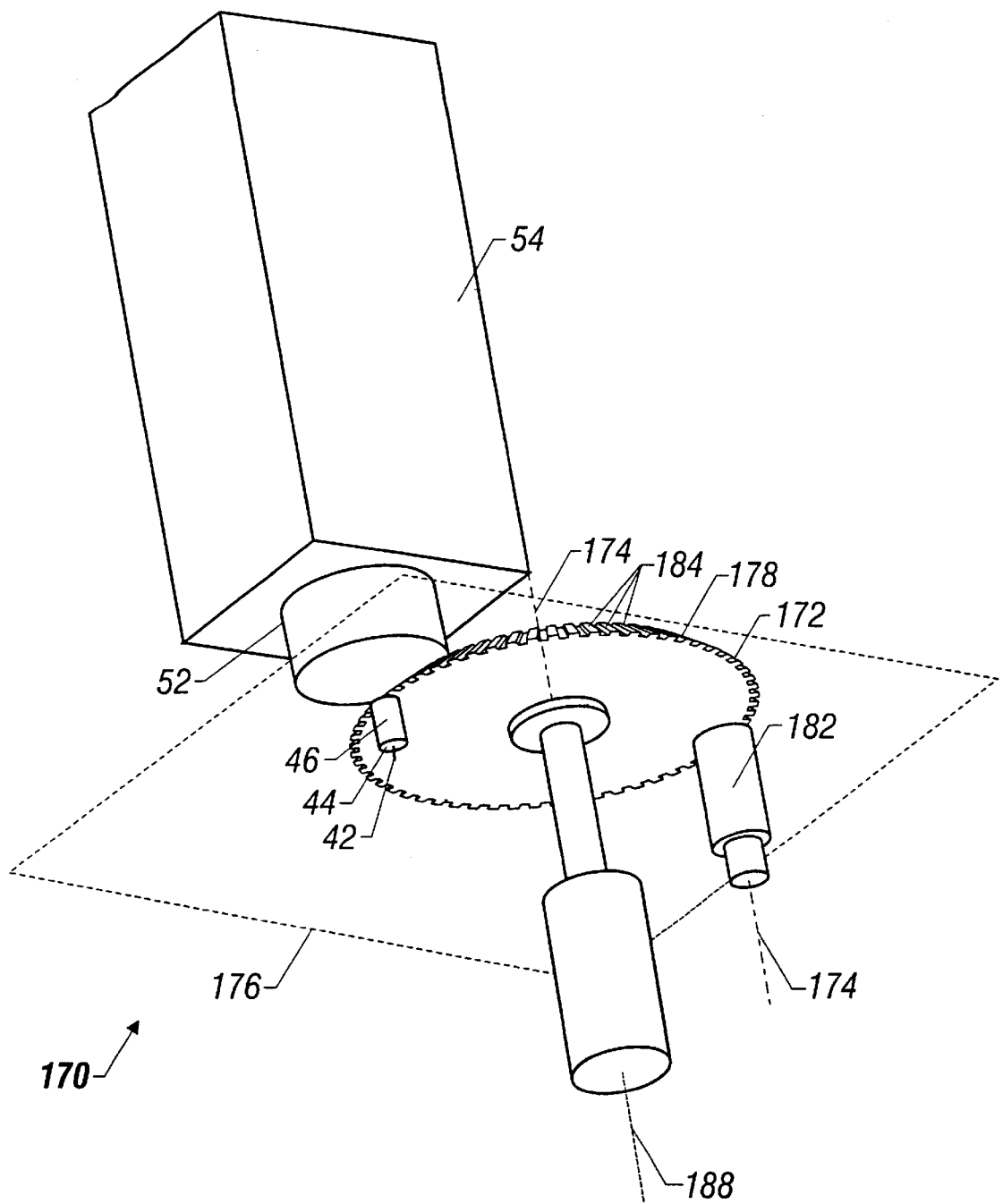
FIGS. 10-A, 10-B and 10-C shows an endoscope with prismatic chopping wheels.
Figure 10B:
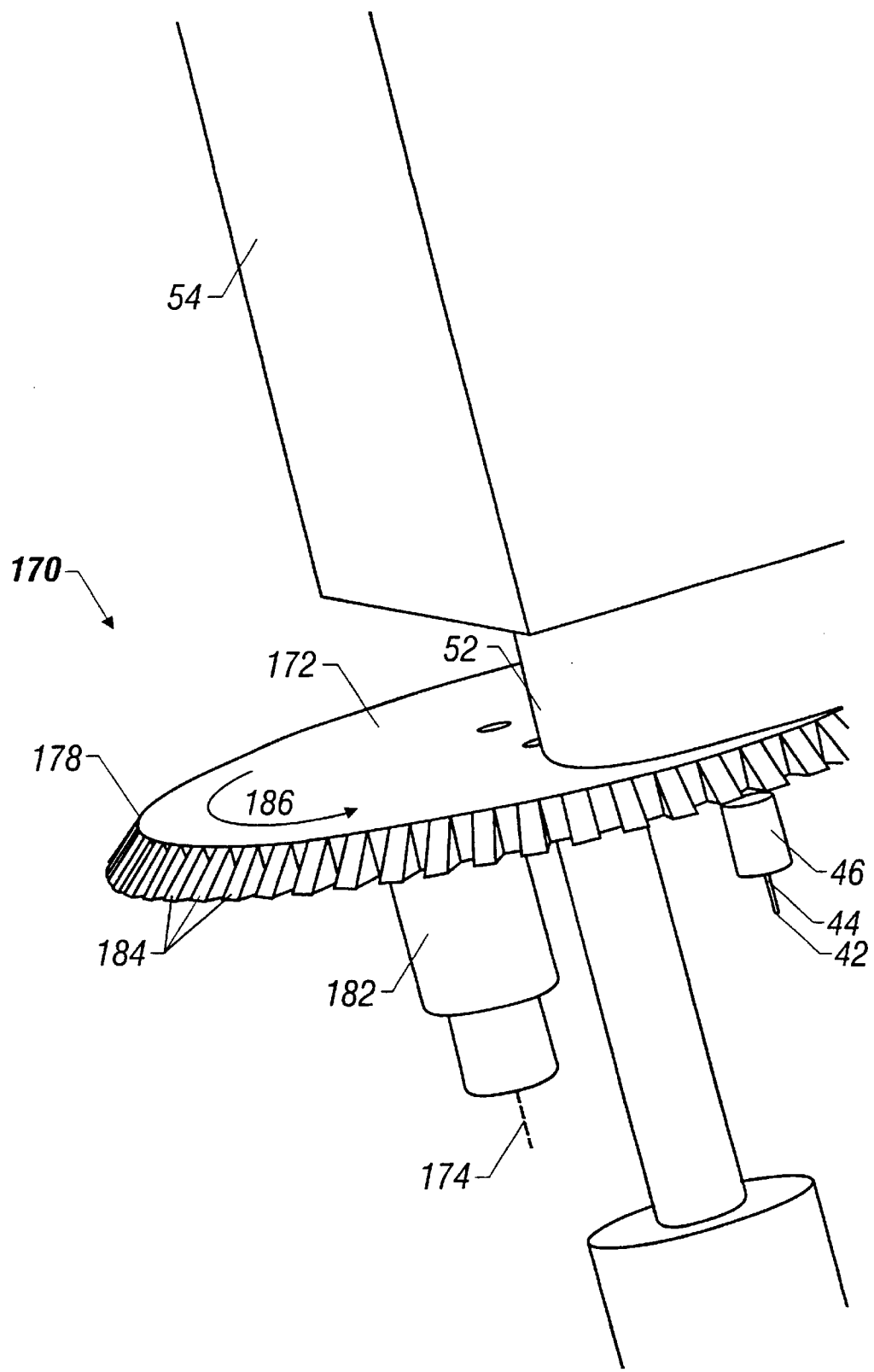
Figure 10C:
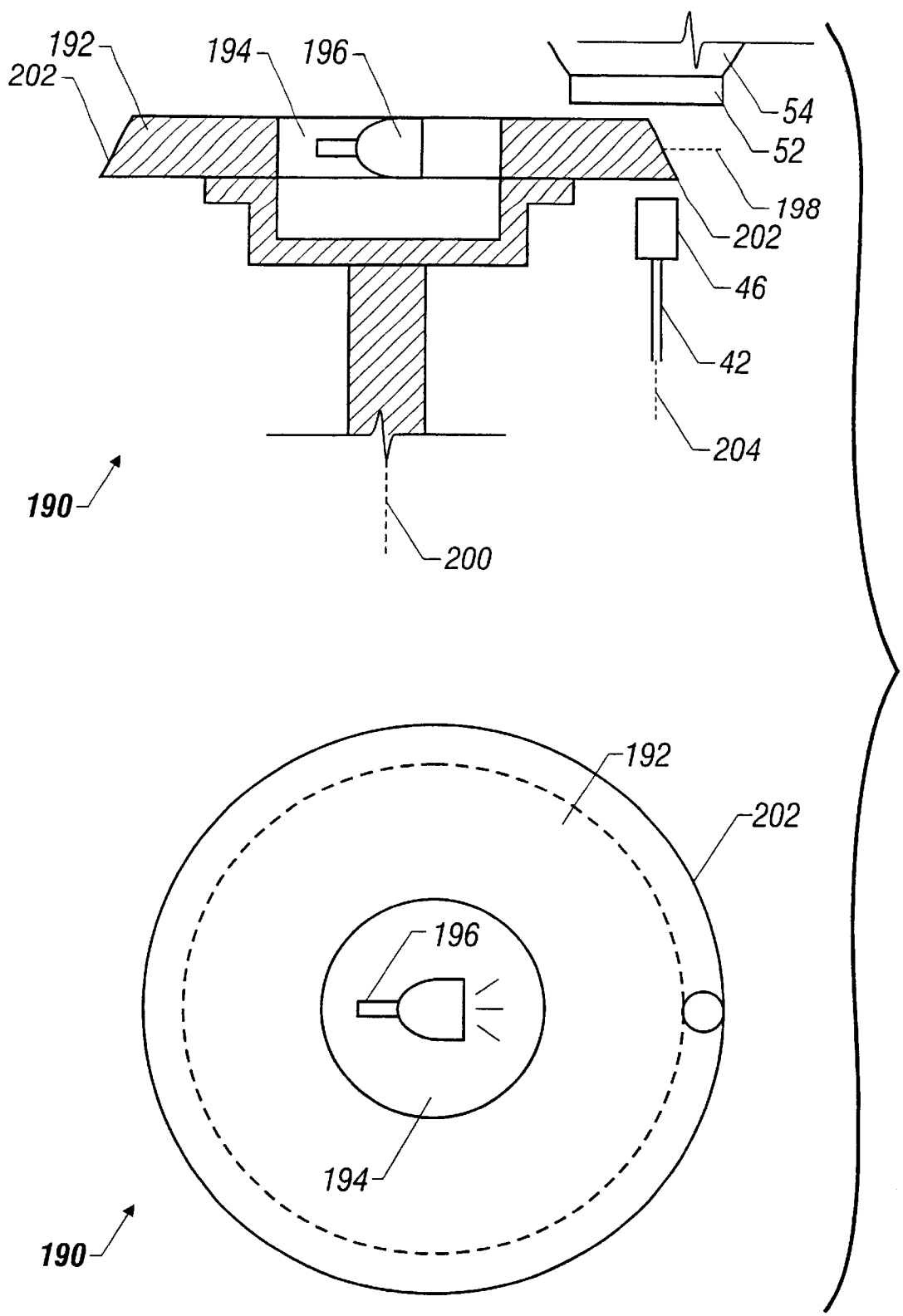
Figure 11A:
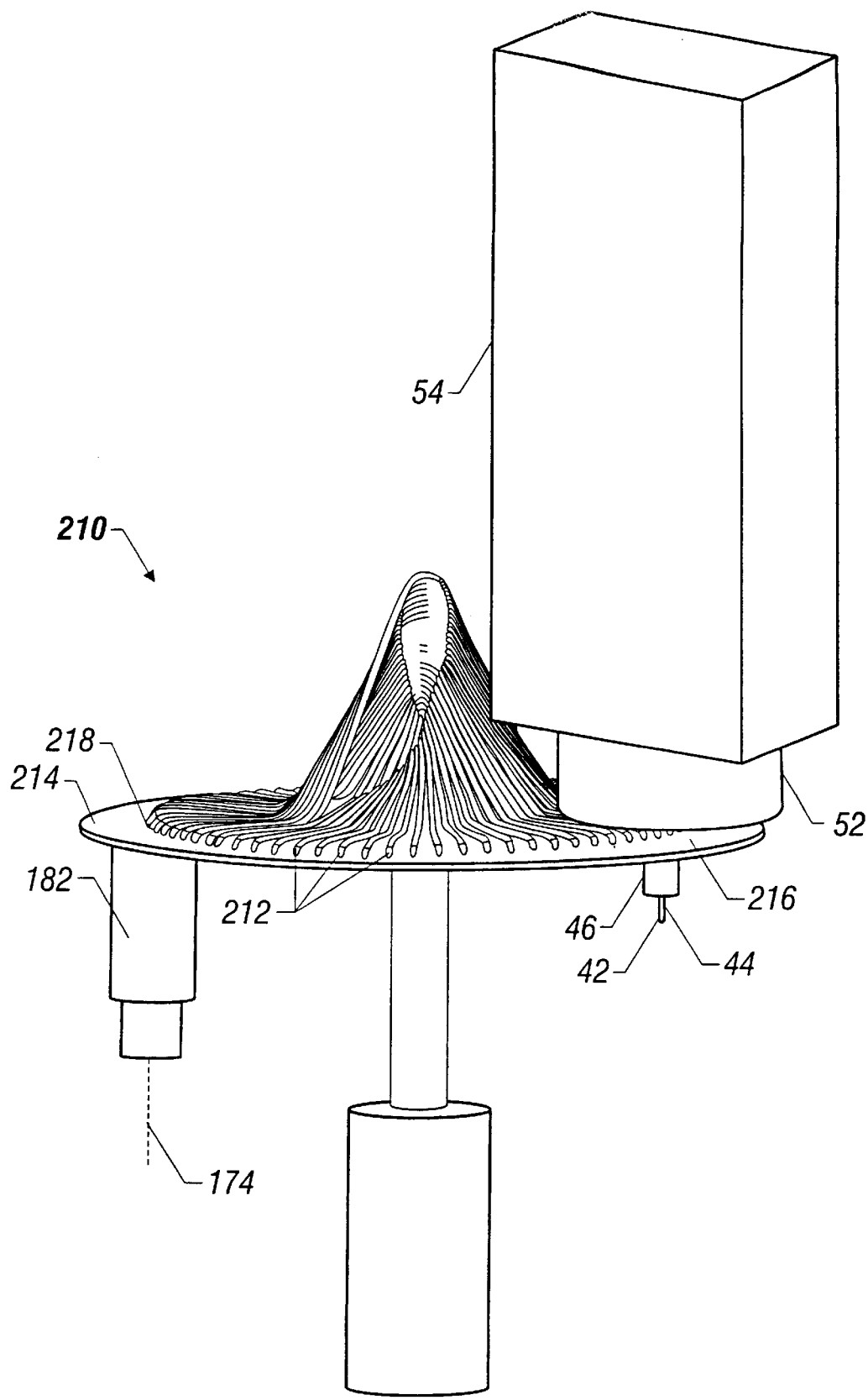
FIGS. 11-A, 11-B and 11-C shows an endoscope with fiber optic guide.
Figure 11B:
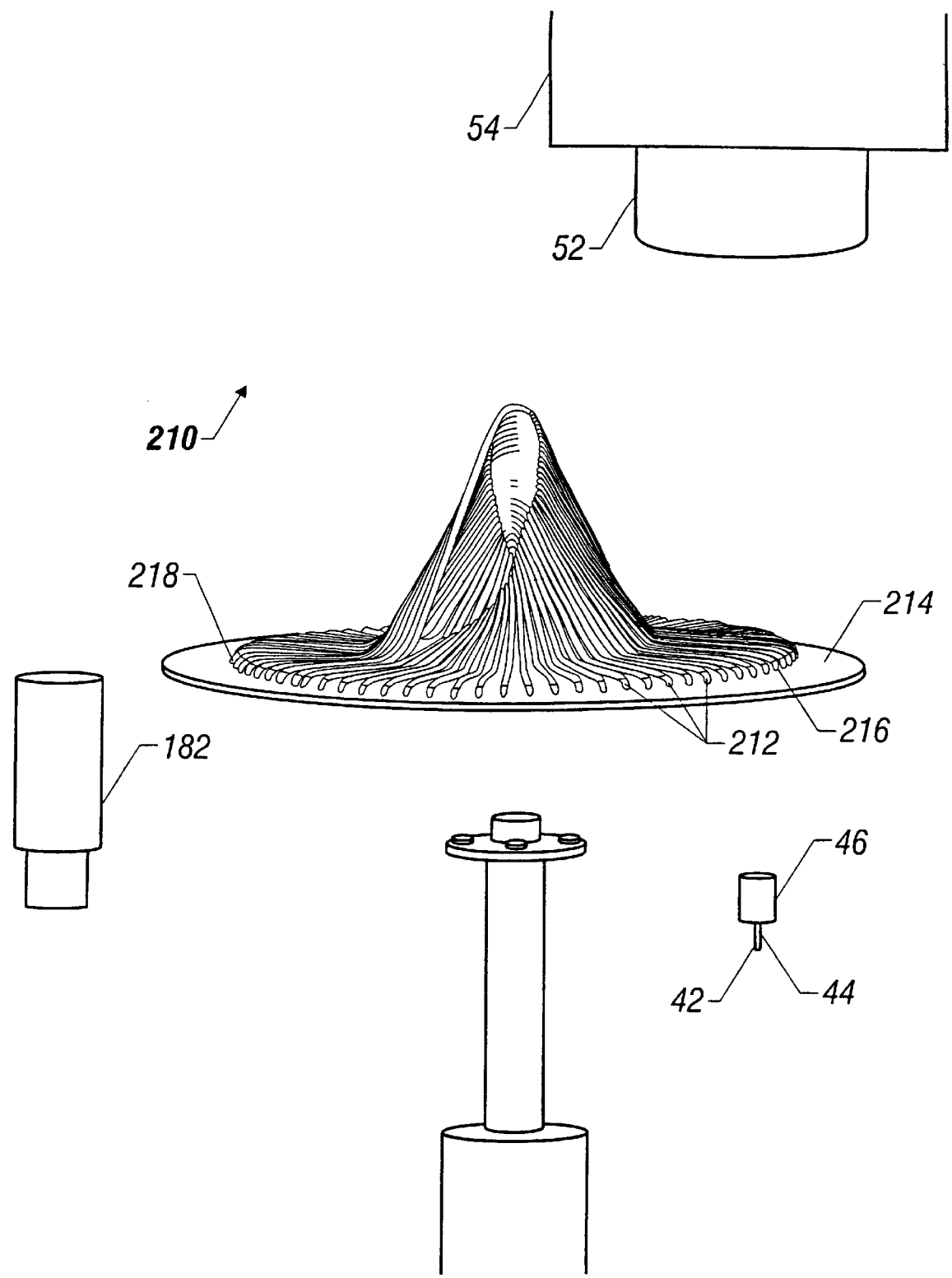
Figure 11C:
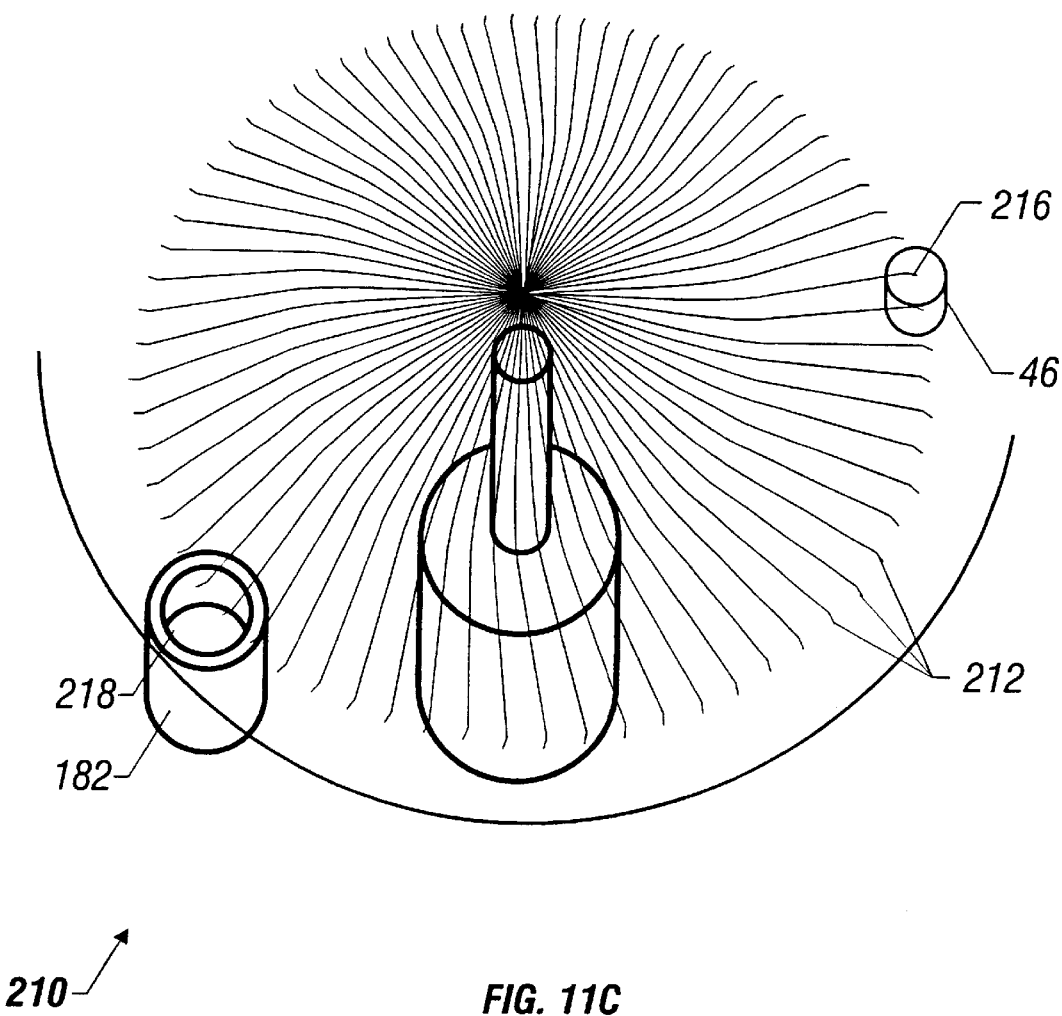
Figure 13:
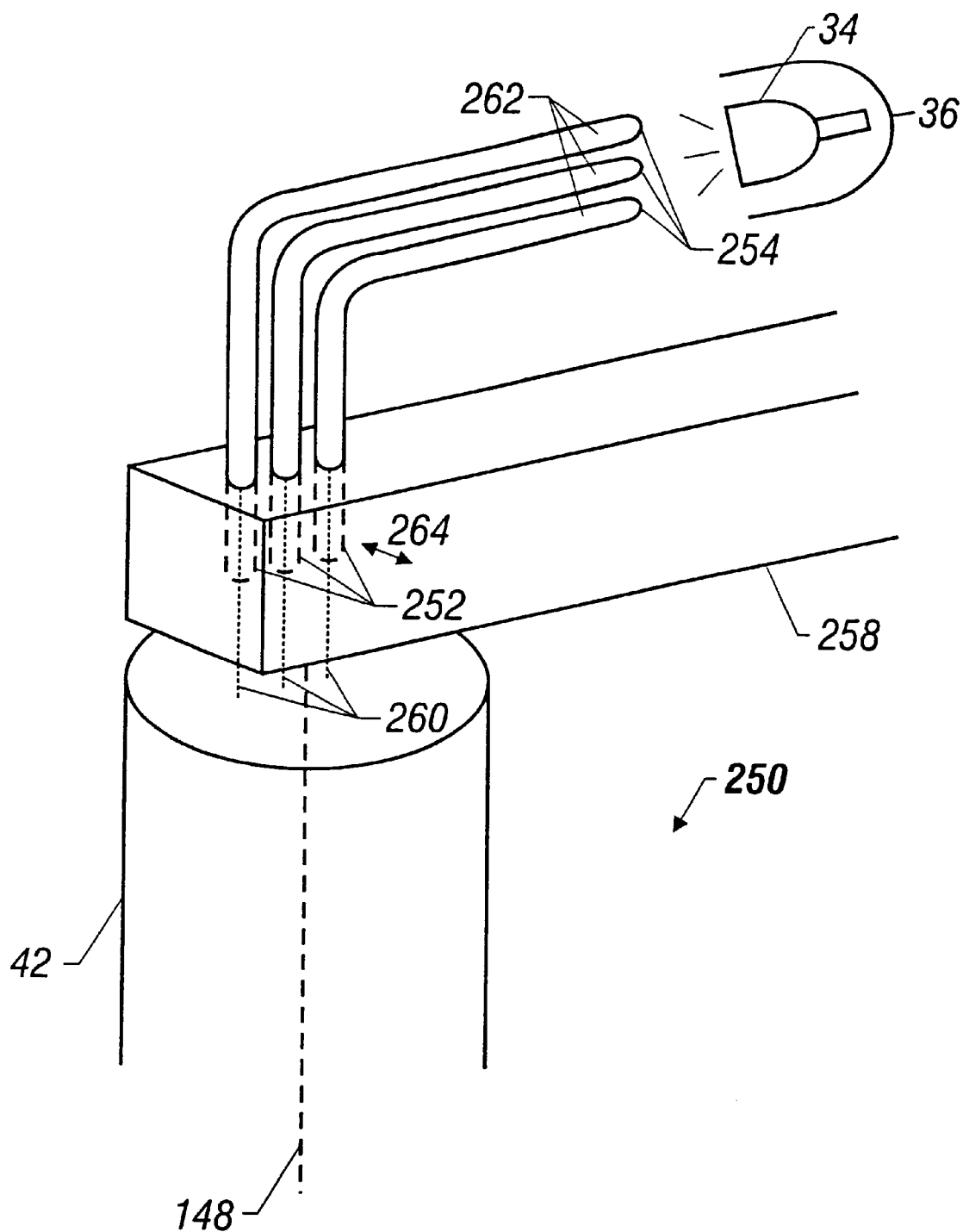
FIG. 13 shows a fiber light conductor mounted to the beam.

Oscillatory Motion With Prismatic Channeler (See FIG. 9-1)

In endoscope 160, one or two prisms 162 oscillate within illumination plane 163 diverting light originating from source 165 from illumination plane 164 into image bundle 42. As shown, illumination plane 164 is normal to bundle axis 166 and coincident with light source 165 and prisms 162.

Prismatic Chopler Wheel (See FIGS. 10-1, 10-2, 10-3)

VERSION 1: In endoscope 170 light is channeled via transparent disk 172 spinning about axis 188, parallel to illumination axis 174 within illumination plane 176. Slightly below outer rim 178 of disk 172 at opposite points across illumination axis 174 are located exiting face 180 of fixed light source 182 and proximal end 44 of imaging bundle 42.

In outer rim 178 of transparent disk 172 are cut a plurality of prismatic protrusions 184. When aligned over light source 182, prismatic protrusions 184 divert light from source 182 into illumination plane 176. Disk 172 rotates in illumination plane 176. When located above image bundle 42, prismatic protrusions 184 channel light out of illumination plane 176 and into image bundle 42. Disk 172 allows light transmission between the point at which it is received from light source 182 to its target on image bundle 42. Transparent disk 172 rotates in direction 186 about axis 188 in illumination plane 176.

The image transmitted from image bundle 42 through the spaces not occupied by the protrusions may be viewed or recorded by recording device 54. The viewed image is similar to that seen looking through a rotary fan or a propeller.

VERSION 2: In endoscope 190 (FIG. 10-3), transparent disk 192 is identical to transparent disk 172 except that its center has been removed to allow clearance space 194 for light source 196. As in the case of endoscope 170, transparent disk 192 spins within illumination plane 198 about illumination axis 200. Light enters image bundle 42 through the same means of prismatic protrusions (not shown). located at rim 202 of transparent disk 192. What differs in this version is the location of light source 196. Light source 196 is located within illumination plane 198 at the illumination axis 200, i.e., in the center hole 194 at the center of the disk described above. Light source 196 is aimed directly at bundle axis 204. Light is transmitted from the center of the disk to the disk's rim 202 where is then diverted into GRIN lens 46, thence into image bundle 42, by-means of the channeling protrusions (not shown).

Fiber Light Channels Mounted to a Wheel (See Drawings 11-1, 11-2, 11-3)

Endoscope 210 is similar to endoscopes 160 and 170 described above with the following differences. In the place of prismatic protrusions 184, a plurality of fiber optic light guides 212 are positioned over transparent disk 214. At a given instant, when one end 216 of one of fiber optic guides 212 is located over image bundle 42, the other end 218 of fiber optic guide 212 is located above light source 182. In this case then, the actual light channeler is light guide 212. Transparent disk 214 acts as a carrier of the light guides, and means to precisely position them. In this embodiment, recording device 54 receives the image from bundle 42 through transparent disk 214 between fiber optic guides 212.

Fiber Light Channelers Mounted to Beam (See Drawing 12-1)

In endoscope 230 light channeling consists of fiber optic light guide 232 partially embedded within cantilever beam 234. Cantilever beam 234 oscillates within illumination plane 235 about image bundle axis 166. Light may be focused from light source 236 into light guide 232 by means of a light focusing device 238, such as converging lens(es). Light then travels through light guide 232, which is mounted to oscillating beam 234, to a light channeler 240, such as prism. Channeler 240 is located in illumination plane 235 at bundle axis 166. Light entering channeler 240 from light guide 232 is diverted into image bundle 42. In endoscope 230, light may enter directly into imaging bundle 42 from the channeler instead of entering a GRIN lens (not shown). If a GRIN lens is employed the light may be further focused before entering the image bundle. Beam oscillation is accomplished by means of beam driver or actuator 242.

Fiber Light Conductor Mounted to Beam (See Drawing 13)

Endoscope 250 is a further variation of the embodiment depicted by endoscope 230. Except for the details contained herein, it will be appreciated that other elements not depicted are the same. In endoscope 250, distal portions 252 of at least one fiber optic guide 254 are embedded within a distal portion 256 of beam 258. Axes 260 of portions 252 are parallel with respect to each other. Beam 258 is disposes so that axes 260 extend into image bundle 42 and such that axes 260 are parallel to axis 148 of image bundle 42. Proximal ends 262 of fiber optic guides open toward light source 34. Light from light source 34 may be focused by light focusing device 36. In use, distal portion 256 oscillates as shown by arrow 264 generally perpendicular to axis 148, thereby directing light over a variable portion of image bundle 42.

FABRICATION

Fabrication techniques employed in producing above devices include but are not limited to conventional large scale fabrication techniques, such as milling, turning, molding, etc. Also less conventional means of fabrication may be employed such as surface micro-machining, and other techniques exploited in the production of microelectromechanical systems (MEMS).

Other embodiments are within the following claims. For example, any device which receives light from a light source and channels it into a discrete portion of the image bundle could be used as the light channeler.

It will be appreciated that the GRIN lens is used primarily for magnification, and may or may not be present with any particular embodiment in which there is a need or desire for magnification.

While the preferred embodiment describes using light to illuminate the area to be imaged, it should be understood that other forms of energy, including, for example, UV, IR and ultrasound, could be used for this imaging.

What is claimed is:

1. A method of fiber optic endoscopy in which bundle of coherent optical fibers extends from a distal end to a proximal end of an endoscope, the method comprising:

conveying an optical image from the distal end to the proximal end through filaments of the fiber optic bundle;

concurrently with transmission of the image from the distal end to the proximal end, transmitting illumination light from the proximal end to the distal end of the fiber optic bundle through a fraction of the optical fibers that are conveying the optical image from the distal end to the proximal end;

wherein the fraction of the optical fibers are notched between the distal and proximal end, the method further including passing illuminating light through the notches into the notched fibers to the distal end, image light concurrently moving through the notched fibers from the distal end to the proximal end with at least a portion of the image light passing the notch.

2. A method of fiber optic endoscopy in which a bundle of coherent optical fibers extends from a distal end to a proximal end of an endoscope, the method comprising:

conveying an optical image from the distal end to the proximal end through filaments of the fiber optic bundle;

concurrently with transmission of the image from the distal end to the proximal end, transmitting illumination light from the proximal end to the distal end of the fiber optic bundle through a fraction of the optical fibers that are conveying the optical image from the distal end to the proximal end;

wherein the fraction of the optical fibers which carry illumination light changes as the optical image continues to be transmitted from the distal end to the proximal end; and wherein the fraction of optical fibers which carry the illumination light change in a circular pattern.

3. A method of fiber optic endoscopy comprising:

passing images from a distal end of a bundle of optical fibers to a proximal end;

between the distal and proximal ends, passing illuminating light through notches in at least some of the optical fibers, into and through the notched optical fibers to the distal end to provide illumination light;

converting the optical image passed to the proximal end of the fiber optic bundle into an electronic image representation.

4. A fiber optic endoscope comprising:

a coherent fiber optic bundle extending from a distal end to a proximal end;

a light source for sending illumination light to the distal end of the fiber optic bundle through a fraction of the fibers of the fiber optic bundle;

an opto-electrical transducer for converting optical images conveyed from the distal to the proximal end of the coherent fiber optic bundle into an electronic image representation;

notches in a plurality of the optical fibers between their distal and proximal ends; and said light source transmitting the illumination light into the notched fibers through the notch and along the notched fibers to the distal end.

5. A fiber optic endoscope comprising:

a coherent fiber optic bundle extending from a distal end to a proximal end;

a light source for sending illumination light to the distal end of the fiber optic bundle through a fraction of the fibers of the fiber optic bundle;

an opto-electrical transducer for converting optical images conveyed from the distal to the proximal end of the coherent fiber optic bundle into an electronic image representation;

said light source illuminating a fraction of the optical fibers adjacent the proximal end, the source illuminating light partially obstructing the opto-electrical transducer; and a mechanism for causing relative motion between the proximal end of the fiber optic bundle and the illumination light source such that a portion of the optical image blocked by the illumination light source changes during an imaging procedure such that all optical fibers of the fiber optic bundle contribute to the electronic image representation.

6. The fiber optic endoscope as set forth in claim 5 wherein the illumination light source includes one of a mirror and a prism movably mounted adjacent the proximal end of the fiber optic bundle.

* * * * *